(12) United States Patent
Sato et al.

(10) Patent No.: US 6,641,585 B2
(45) Date of Patent: Nov. 4, 2003

(54) BONE CONNECTING TOOL AND CONNECTING MEMBER THEREOF

(75) Inventors: Shigenobu Sato, Hokkaido (JP); Yutaka Nohara, Saitama-ken (JP); Kazuya Oribe, Tokyo (JP); Hiroshi Takamido, Aichi-ken (JP)

(73) Assignee: Showa Ika Kohgyo Co., Ltd., Nagoya (JP)

( * ) Notice: Subject to any disclaimer, the term of this patent is extended or adjusted under 35 U.S.C. 154(b) by 75 days.

(21) Appl. No.: 09/956,121

(22) Filed: Sep. 20, 2001

(65) Prior Publication Data

US 2002/0040223 A1 Apr. 4, 2002

(30) Foreign Application Priority Data

Sep. 22, 2000 (JP) ........................................ 2000-289291

(51) Int. Cl.[7] ................................................. A61B 17/56
(52) U.S. Cl. ............................................................. 606/61
(58) Field of Search ............................ 606/61, 72, 73, 606/65, 53, 70

(56) References Cited

U.S. PATENT DOCUMENTS

| | | | |
|---|---|---|---|
| 5,306,275 A | * | 4/1994 | Bryan ........................ 606/61 |
| 5,395,370 A | | 3/1995 | Müller et al. |
| 5,468,241 A | * | 11/1995 | Metz-Stavenhagen et al. ... 606/61 |
| 5,498,262 A | | 3/1996 | Bryan |
| 5,520,689 A | | 5/1996 | Schläpfer et al. |
| 5,545,165 A | * | 8/1996 | Biedermann et al. ......... 606/61 |
| 5,725,582 A | | 3/1998 | Bevan et al. |
| 5,810,817 A | * | 9/1998 | Roussouly et al. ........... 606/61 |
| 5,947,965 A | | 9/1999 | Bryan |
| 6,077,262 A | | 6/2000 | Schläpfer et al. |
| 6,077,263 A | | 6/2000 | Ameil et al. |
| 6,096,039 A | * | 8/2000 | Stoltenberg et al. .......... 606/61 |
| 6,132,430 A | * | 10/2000 | Wagner ....................... 606/61 |
| 6,387,097 B1 | * | 5/2002 | Alby ........................... 606/61 |

FOREIGN PATENT DOCUMENTS

| EP | 0743045 | | 11/1996 | |
|---|---|---|---|---|
| WO | WO 95/06440 | * | 3/1995 | ................... 606/61 |
| WO | WO 98/41160 | * | 9/1998 | ................... 606/61 |

* cited by examiner

Primary Examiner—Pedro Philogene
(74) Attorney, Agent, or Firm—Greenblum & Bernstein, P.L.C.

(57) ABSTRACT

Bone connecting tool for interconnecting vertebral bodies. The bone connecting tool includes a rod member having a first hook portion. A rod engaging member is fixed to the rod member having a second hook portion. A projection portion for eating into an arch of vertebrae is provided in the second hook portion.

9 Claims, 3 Drawing Sheets

BONE CONNECTING TOOL AND CONNECTING MEMBER THEREOF

BACKGROUND OF THE INVENTION

1. Field of the Invention

The present invention relates to a bone connecting tool for connecting a corpus vertebrae and a connecting member used in the bone connecting tool, and more particularly to a bone connecting tool which can properly and stably keep a positional relationship between the corpus vertebrae and the connecting tool, and a connecting member thereof

2. Description of the Related Art

In the case of connecting a corpus vertebrae such as a lumbar vertebrae or the like, there is executed a method of screwing and inserting respective screws to apart bodies of vertebrae in a corpus vertebrae, respectively engaging one end side and another end side of a rod with engagement grooves formed in a head portion of the respective screws and fixing both end sides of the rod to both screws by a fixing screw. Further, there is employed a structure of supporting and fixing both end portions of the rod by a hook member provided with a hook portion freely hooked to an arch of vertebrae in the corpus vertebrae.

In the structure of screwing and inserting the screws to the bodies of vertebrae in the corpus vertebrae and supporting both end portions of the rod by the screws, it is necessary to screw and insert the screw to the corpus vertebrae in an accurate direction and at an accurate depth, so that there is a problem that it is hard to screw and insert the screw.

In the structure of hooking the hook portion of the hook member to the arch of vertebrae in the corpus vertebrae and supporting and fixing both end portions of the rod by the respective hook member, it is unnecessary to screw and insert the screw to the corpus vertebrae. However, since the hook portion in the hook member is simply hooked to the arch of vertebrae, there is a problem to be improved in view of improving a stability.

SUMMARY OF THE INVENTION

The present invention is made by taking the problems described above into consideration, according to a first aspect of the present invention, there is provided a bone connecting tool for interconnecting vertebral bodies comprising: a rod engaging member attachable to an arch of vertebrae in a corpus vertebrae; and a rod member having a rod portion freely fixed to the rod engaging member, wherein a projection portion for eating into the arch of vertebrae is provided in the second hook portion provided in the rod engaging member.

Moreover, the structure may be made such that the rod member is provided with a processus spinosus in the corpus vertebrae or a first hook portion freely hooked to the arch of vertebrae in one end portion thereof, and a projection portion for eating into the processus spinosus or the arch of vertebrae is provided in the first hook portion.

Moreover, there is provided a bone connecting tool comprising: a hook member freely hooked to an arch of vertebrae in a corpus vertebrae; and a connecting member having a rod portion freely fixed to the rod engaging member, wherein the rod member is provided with a processus spinosus in the corpus vertebrae or a first hook portion freely hooked to the arch of vertebrae in one end portion thereof, and a projection portion for eating into the processus spinosus or the arch of vertebrae is provided in the first book portion.

Moreover, the rod member in the structure described above is structured so as to have a substantially V shape or J shape, and is provided with a projection portion inside a bent portion.

DETAILED DESCRIPTION OF THE PREFERRED EMBODIMENTS

Hereinafter, a description of embodiments according to the present invention will be given with reference to the accompanying drawings.

<First Embodiment>

Figure 1:
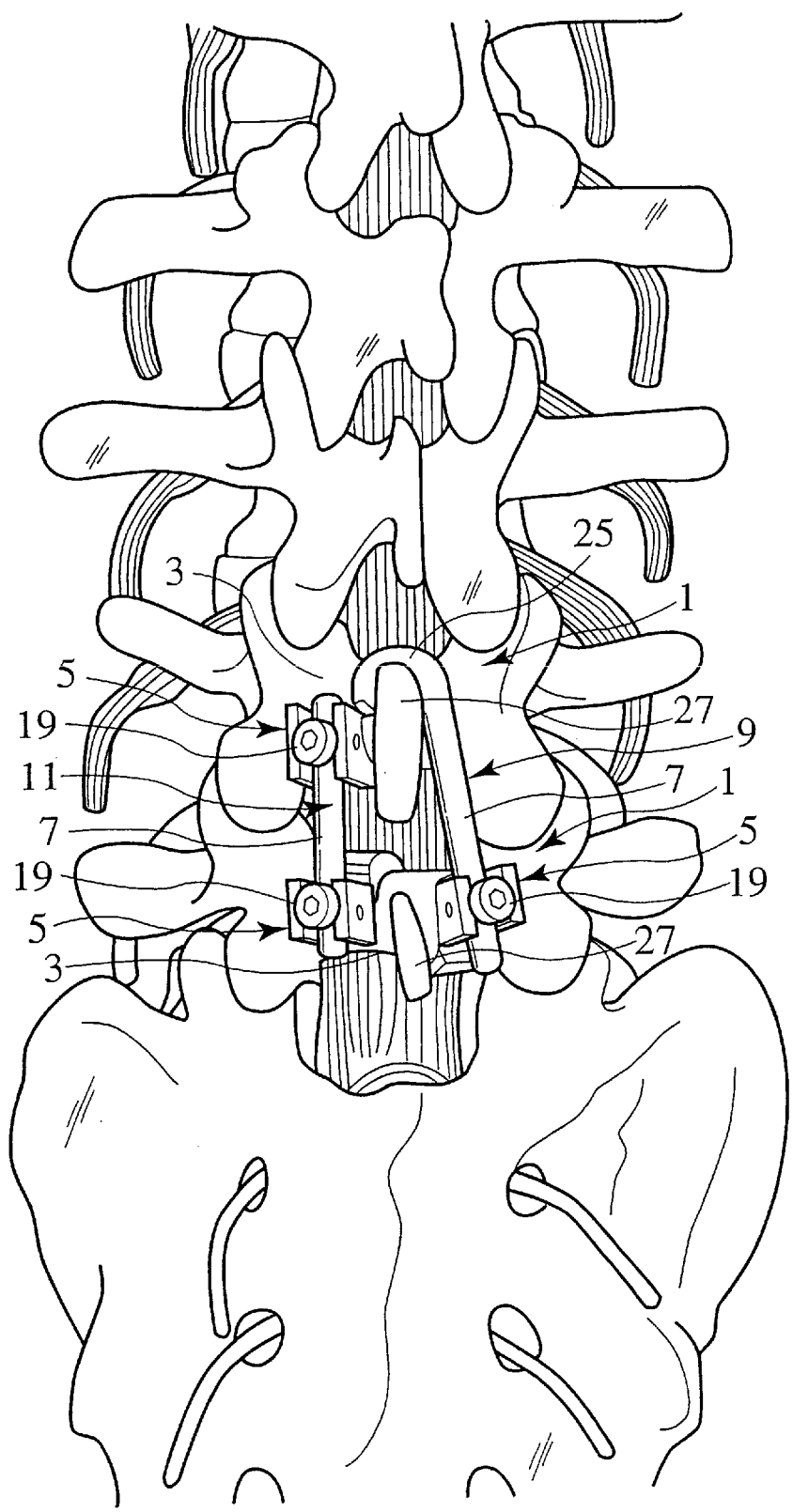
FIG. 1 is a schematic view showing a use example of a bone connecting tool according to a first embodiment of the present invention.
Figure 2:
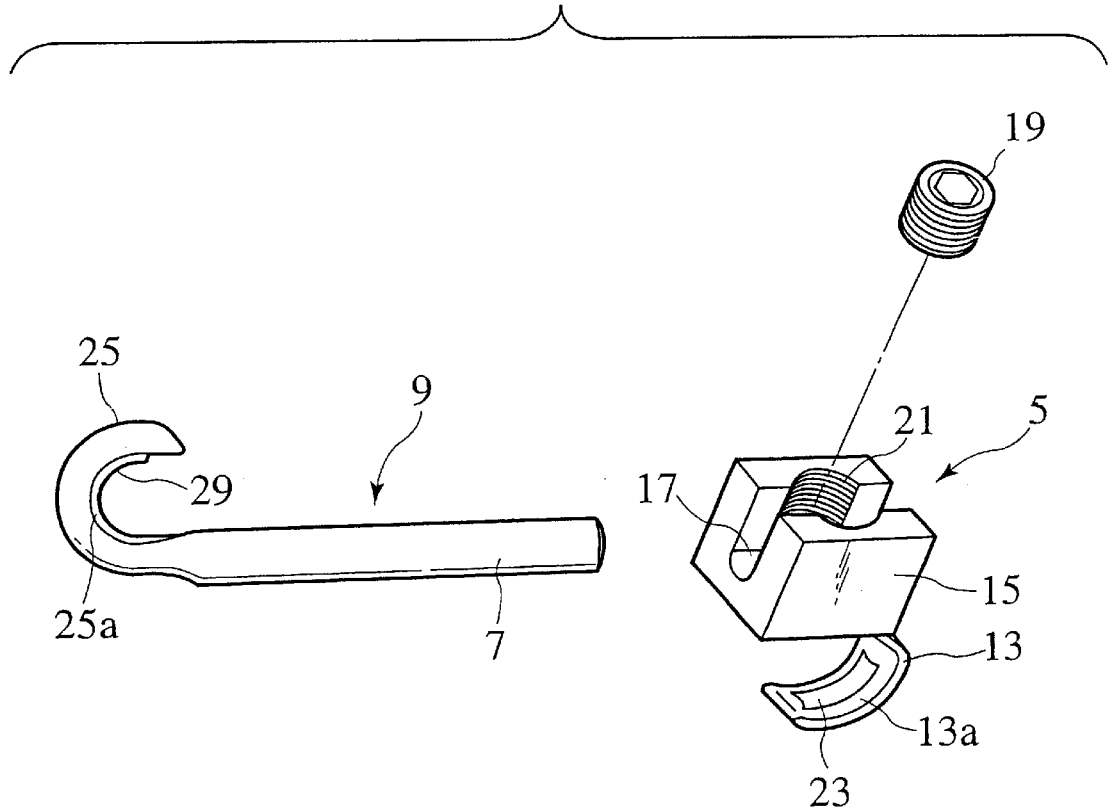
FIG. 2 is a perspective explanation view of the bone connecting tool described above.

FIG. 1 is a view showing a first embodiment according to the present invention. A bone connecting tool for interconnecting vertebral bodies is provided with a rod members 9 and 11 having a rod engaging member 5 freely mounted to an arch of vertebrae 3 in a corpus vertebrae 1 and a rod portion 7 freely fixed to the rod engaging member 5. The rod engaging member 5 is, as shown in FIG. 2, provided with a curved second hook portion 13 freely hooked to the arch of vertebrae 3 and a rod fixing potion 15 freely fixing the rod portions 7 of the rod members 9 and 11.

More particularly, the rod fixing portion 15 is provided with an engagement groove 17 freely engaging the rod portions 7 of the rod members 9 and 11. A screw portion 21 screwing a fixing screw 19 which freely presses and fixes the rod portion 7 engaged with the engagement groove 17 in an immobile state is formed in both sides of the engagement groove 17.

The second hook portion 13 is integrally provided in the rod fixing portion 15 in an opposite side in an opening direction of the engagement groove 17 and the screw portion 21 (on a back surface in the case that the engagement groove 17 is a front surface), and a center in a width direction of the second hook portion 13 coincides with a center in a width direction of the engagement groove 17. A projection portion 23 for eating into the arch of vertebrae 3 of the corpus vertebrae is formed in a center portion in the width direction of the second hook portion 13.

It is sufficient that the projection portion 23 has a function of eating into the arch of vertebrae 3 at a time of hooking the second hook portion 13 to the arch of vertebrae 3, for example, the projection 23 may be an acanthous projection, however, in the present embodiment, is formed as a linear protrusion along a curve of a curved inner surface 13a in the second hook portion 13. In this case, in the illustrated embodiment, the projection portion 23 is exemplified by one protrusion, however, a plurality of protrusions may be employed, or an inclined protrusion or a plurality of crossed protrusions may be employed, so that various kinds of structures can be employed as an aspect of the projection portion 23.

The rod member 9 is, as shown in FIG. 2, structured such as to be provided with the rod portion freely engaging with the engagement groove 17 of the rod engaging member 5 in one end portion, and provided with a first hook portion 25 in another end portion, and is schematically formed in a substantially J shape. The first hook portion 25 is curved so as to be hooked to the arch of vertebrae 3 in the corpus vertebrae 1 or the processus spinosus 27 (refer to FIG. 1), and a projection portion 29 is provided on a curved inner surface 25a of the first hook portion 25 in the same manner as the second hook portion 13 in the rod engaging member 5. Since it is sufficient that the projection portion 29 has the same structure as that of the projection portion 23 of the second hook portion 13, a detailed description thereof will be omitted.

Since the rod member 11 shown in FIG. 1 is a simple linear rod engaged with and supported to the engagement groove 17 in the rod engaging member 5 at both end portions, a detailed description thereof will be omitted.

In the structure described above, as shown in FIG. 1, it is possible to integrally bond and connect the corpuses vertebrae 1 apart from each other by the rod engaging member 5 and the rod member 9 by hooking the second hook portion 13 of the rod engaging member 5 to the arch of vertebrae 3 in one corpus vertebrae, hooking the first hook portion 25 in the rod member 9 to the processus spinosus 27 in another corpus vertebrae apart therefrom, engaging the rod portion 7 of the rod member 9 with the engagement groove 17 of the rod engaging member 5 and pressing and fixing by the fixing screw 19, and it is possible to prevent the corpuses vertebrae 1 from moving in an apart direction to each other. In addition, the diameter of the rod portion 9 is smaller than the width of the engagement groove 17. So, the rod member 11 can rotate the inside of the engagement groove 17 freely until it fixes a rod portion 9 with the fixing screw 19.

When hooking the second hook portion 13 in the rod engaging member 5 to the arch of vertebrae 3 in the corpus vertebrae in the manner as described above, the projection portion 23 provided in the second hook potion 13 eats into the arch of vertebrae 3 described above, and when hooking the first hook portion 25 of the rod member 9 to the processus spinosus 27, the projection portion 23 provided in the first hook portion 25 eats into the processus spinosus 27. Accordingly, it is possible to stably mount the rod engaging member 5 with respect to a fixed position of the arch of vertebrae 3 in an immobile state, and it is possible to stably mount the first hook portion 25 of the rod member 9 with respect to a predetermined position of the processus spinosus 27. That is, at a time of connecting the apart corpuses vertebrae to each other, it is possible to easily and stably execute the operation by the rod engaging member 5 and the rod member 9.

In the case of using the rod member 11, as shown in FIG. 1, the apart corpuses vertebrae 1 are connected by hooking the second hook portions 13 in the respective rod engaging members 5 to the arches of vertebrae 3 in the corpuses vertebrae 1 apart from each other so that a pair of rod engaging members 5 are directed to opposite directions to each other, engaging both end portions of the rod member 11 with the engagement grooves 17 in a pair of rod engaging members 5 and fastening and fixing by the fixing screws 19. In addition, the diameter of the rod portion 9 is smaller than the width of the engagement groove 17. So, the rod portion 11 can rotate the inside of the engagement groove 17 freely until it fixes a rod portion 9 with the fixing screw 19.

At this time, the rod member 11 functions so as to protrude, and can prevent the corpuses of vertebrae 1 apart from each other from moving in a direction moving close to each other. In this case, the projection portion 23 provided in the second hook portion 13 in the rod engaging member 5 eats into the arch of vertebrae 3, and keeps a stable state.

<Second Embodiment>

Figure 3:
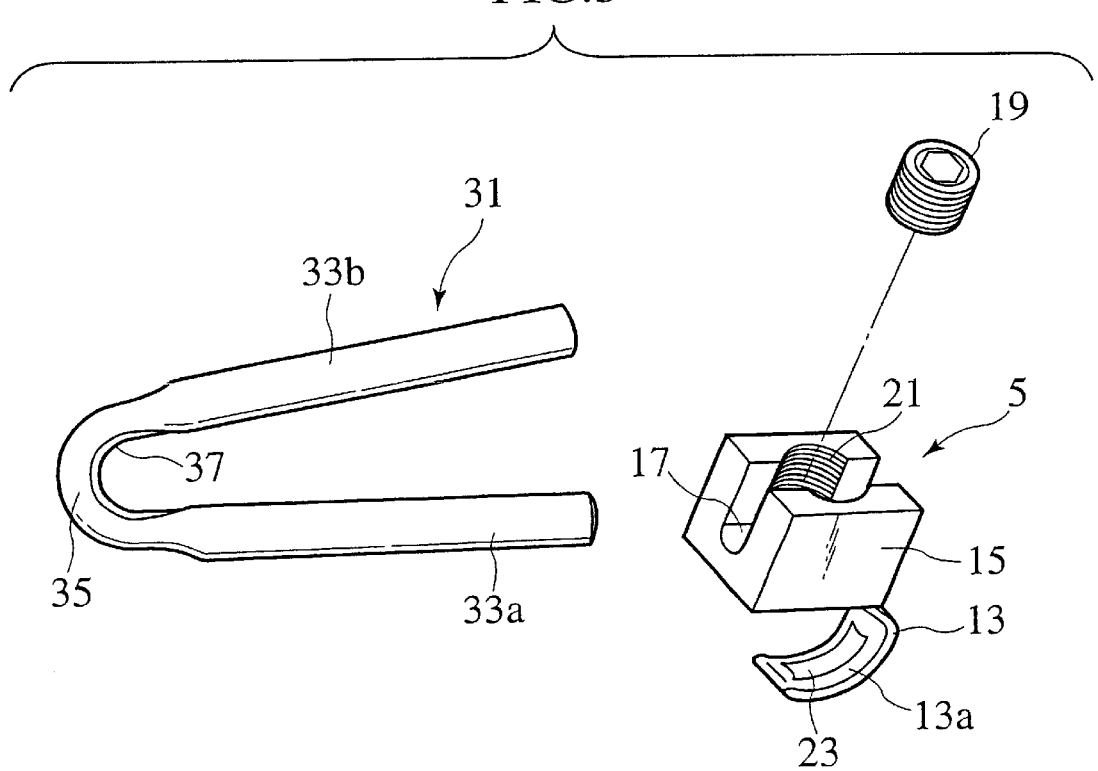
FIG. 3 is a perspective explanation view showing a second embodiment of a connecting member according to the present invention.

FIG. 3 is a view showing a second embodiment according to the present invention. This embodiment is constituted by a rod member 31 formed in a substantially V shape or the like. The rod member 31 is provided with rod portions 33a and 33b corresponding to the rod portion 7 in the rod member 9 in both sides of a bent portion 35 so as to be formed in a U shape or a V shape, and is structured such as to be provided with a projection portion 37 corresponding to the projection portion 29 inside the bent portion 35.

A portion near a front end portion of each of the rod portions 33a and 33b in the rod member 31 is engaged with the engagement groove 17 of the rod engaging member 5 in the same manner as that of the rod portion 7 of the connecting member 9, and fixed by the fixing screw 19. In the case that the rod engaging member 5 can not be mounted to the arch of vertebrae 3 in the corpus vertebrae, the structure can be made such that the screw is screwed and inserted to the corpus vertebrae in the same manner as that of the conventional one and the portion near the front end portion of each of the rod portions 33a and 33b in the rod member 31 is fixed by a head portion of the screw.

The structure is made such that the rod member 31 is formed in the U shape or the V shape as described above and both end portions of the rod member 31 are fixed by the rod engaging member 5, the screw or the like, whereby the rod member 31 can be stably and firmly fixed and it is possible to properly and securely keep the positional relationship between the corpus vertebrae and the bone connecting tool.

The present disclosure relates to subject matter contained in priority Japanese Patent Application No. 2000-289291, filed on Sep. 22, 2000, the contents of which is herein expressly incorporated by reference in its entirety.

What is claimed is:

1. A bone connecting tool for interconnecting vertebral bodies comprising:
   a rod member comprising a first hook portion arranged at one end of the rod member;
   the first hook portion comprising a first projection that is configured to eat into a processus of a corpus vertebrae;
   a rod engaging member fixed to the rod member;
   the rod engaging member comprising a second hook portion; and
   the second hook portion comprising a second projection that is configured to eat into an arch of a vertebrae.

2. A bone connecting tool for interconnecting vertebral bodies according to claim 1, wherein the rod member has a substantially J shape having a bent portion and wherein the first projection is provided inside the bent portion.

3. A bone connecting tool for interconnecting vertebral bodies according to claim 1, wherein the rod member has a substantially V shape having a bent portion and wherein the first projection is provided inside the bent portion.

4. A bone connecting tool for interconnecting vertebral bodies according to claim 1, wherein the second projection portion of the rod engaging member is constituted by at least one groove of protrusion.

5. A bone connecting tool for interconnecting vertebral bodies according to claim 1, wherein the rod engaging member further comprises:
   a body comprising a threaded portion and an engagement groove that engages the rod member; and
   a fixing screw that threads into the threaded portion to press and fix the rod member to the rod engaging member,
   wherein the second hook portion is integrally formed with the body.

6. A bone connecting tool for interconnecting vertebral bodies according to claim 5, wherein a diameter of the rod member is smaller than a width of the engagement groove.

7. A rod member used for connecting vertebral bodies, wherein the rod member is formed in a substantially V shape and is provided with a projection portion that is configured to eat into a processus spinosus, wherein the projection portion is arranged inside a bent portion.

8. A rod member used for connecting vertebral bodies, wherein the rod member is formed in a substantially J shape and is provided with a projection portion that is configured to eat into a processus spinosus, wherein the projection portion is arranged inside a bent portion.

9. A rod engaging member used for connecting vertebral bodies comprising:
- a rod fixing portion comprising a threaded portion and an engagement groove that engages a rod member;
- a fixing screw that threads into the threaded portion to press and fix the rod member to the rod engaging member; and
- a curved hook portion integrally formed with the rod fixing portion; and
- the curved hook portion comprising a projection that eats into an arch of vertebrae.

* * * * *